United States Patent
Aragaki

(10) Patent No.: US 9,916,665 B2
(45) Date of Patent: Mar. 13, 2018

(54) CELL TRACKING DEVICE AND METHOD, AND STORAGE MEDIUM NON-TRANSITORY STORING COMPUTER-READABLE CELL TRACKING PROGRAMS

(71) Applicant: OLYMPUS CORPORATION, Tokyo (JP)

(72) Inventor: Hideya Aragaki, Akishima (JP)

(73) Assignee: OLYMPUS CORPORATION, Tokyo (JP)

(*) Notice: Subject to any disclaimer, the term of this patent is extended or adjusted under 35 U.S.C. 154(b) by 58 days.

(21) Appl. No.: 15/013,033

(22) Filed: Feb. 2, 2016

(65) Prior Publication Data

US 2016/0155239 A1    Jun. 2, 2016

Related U.S. Application Data

(63) Continuation of application No. PCT/JP2014/069558, filed on Jul. 24, 2014.

(30) Foreign Application Priority Data

Aug. 2, 2013 (JP) .................... 2013-161531

(51) Int. Cl.
G06K 9/00 (2006.01)
G06T 7/20 (2017.01)
(Continued)

(52) U.S. Cl.
CPC ........... G06T 7/20 (2013.01); G01N 15/1475 (2013.01); G01N 33/4833 (2013.01);
(Continued)

(58) Field of Classification Search
CPC ............. G06K 9/00; G06T 7/00; G02B 21/00
(Continued)

(56) References Cited

U.S. PATENT DOCUMENTS 7,271,952 B2 * 9/2007 Suzuki ............... G01N 21/6452
250/458.1
8,040,411 B2 * 10/2011 Nakajima ............... G06T 5/009
348/254
8,179,597 B2 * 5/2012 Namba ............... G01N 21/6458
359/383

FOREIGN PATENT DOCUMENTS

JP    2006-209698    8/2006
JP    2008-281720    11/2008
(Continued)

OTHER PUBLICATIONS

International Search Report, dated Oct. 14, 2014, issued in corresponding International Application No. PCT/JP2014/069558.
(Continued)

*Primary Examiner* — Abolfazl Tabatabai
(74) *Attorney, Agent, or Firm* — Andrews Kurth Kenyon LLP

(57) ABSTRACT

A cell tracking device includes first and second image acquisition units, first and second tracking units and an interpolation unit. The first image acquisition unit picks up images of a cell under a short-time exposure condition at points in time to capture short-time exposure images. The second image acquisition unit picks up images of the cell under a long-time exposure condition to capture long-time exposure images, each image of the cell under the long-time exposure condition being picked up within each interval between the points in time. The first tracking unit tracks the cell based upon the short-time exposure images. The second tracking unit tracks the cell based upon the long-time exposure images. The interpolation unit interpolates a tracking result obtained by the second tracking unit with a tracking result obtained by the first tracking unit.

12 Claims, 7 Drawing Sheets

(51) Int. Cl.

| | |
|---|---|
| *G02B 21/36* | (2006.01) |
| *G01N 15/14* | (2006.01) |
| *G01N 33/483* | (2006.01) |
| *G06K 9/62* | (2006.01) |
| *G06T 7/00* | (2017.01) |
| *H04N 5/235* | (2006.01) |
| *H04N 5/247* | (2006.01) |
| *G02B 21/00* | (2006.01) |
| *G06T 7/246* | (2017.01) |
| *H04N 5/225* | (2006.01) |
| *G02B 21/16* | (2006.01) |

(52) U.S. Cl.
CPC ....... *G02B 21/0056* (2013.01); *G02B 21/365* (2013.01); *G02B 21/367* (2013.01); *G06K 9/00127* (2013.01); *G06K 9/6202* (2013.01); *G06T 7/0012* (2013.01); *G06T 7/248* (2017.01); *H04N 5/2351* (2013.01); *H04N 5/247* (2013.01); *G02B 21/16* (2013.01); *G06T 2207/10016* (2013.01); *G06T 2207/10056* (2013.01); *G06T 2207/10064* (2013.01); *G06T 2207/20016* (2013.01); *G06T 2207/20101* (2013.01); *G06T 2207/20152* (2013.01); *G06T 2207/20161* (2013.01); *G06T 2207/30024* (2013.01)

(58) Field of Classification Search
USPC ................ 382/103, 107, 236; 348/154, 155, 348/169–172, 352
See application file for complete search history.

(56) References Cited

FOREIGN PATENT DOCUMENTS

| | | |
|---|---|---|
| JP | 2009-082036 | 4/2009 |
| JP | 2010-014964 | 1/2010 |
| JP | 2011-008126 | 1/2011 |
| JP | 2013-050667 | 3/2013 |

OTHER PUBLICATIONS

Written Opinion, dated Oct. 14, 2014, issued in corresponding International Application No. PCT/JP2014/069558.

English translation of International Preliminary Report on Patentability, dated Feb. 11, 2016, and Written Opinion, dated Oct. 14, 2014, from corresponding International Application No. PCT/JP2014/069558.

\* cited by examiner

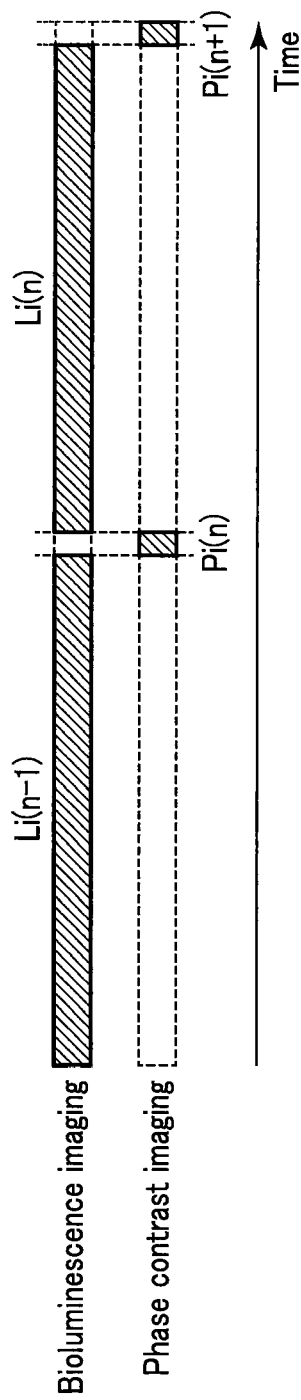
F I G. 3

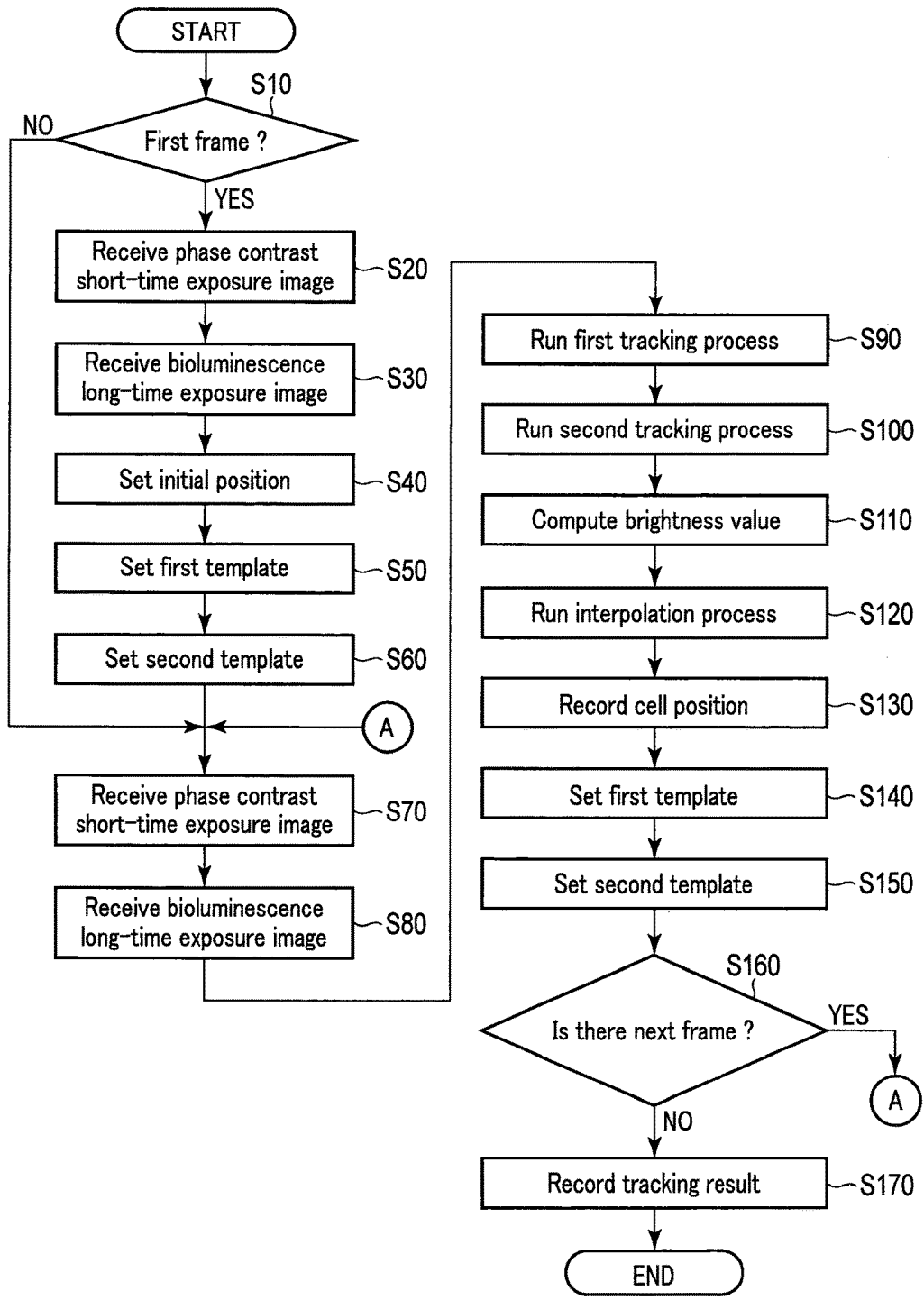
F I G. 4

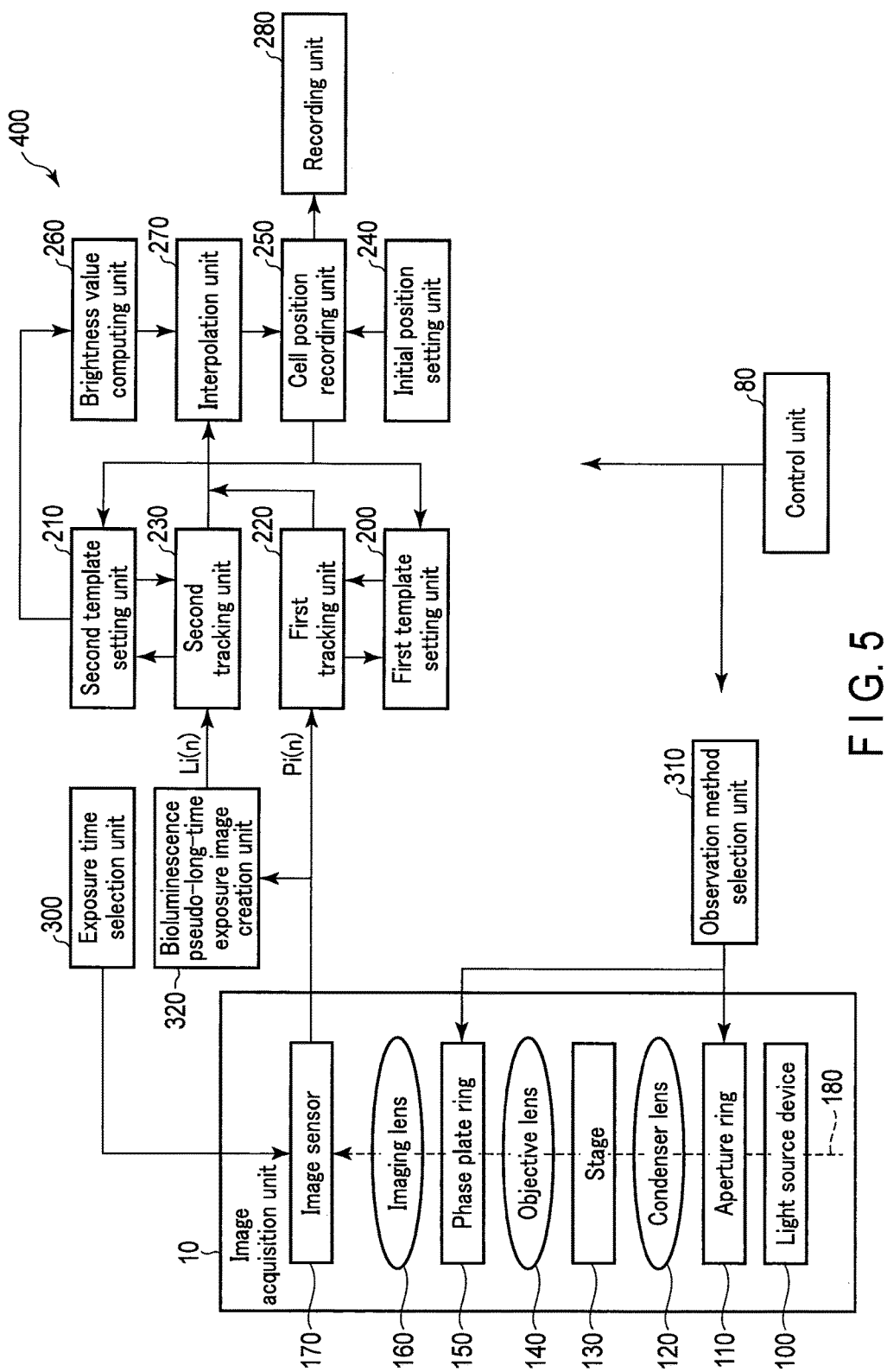
F I G. 5

CELL TRACKING DEVICE AND METHOD, AND STORAGE MEDIUM NON-TRANSITORY STORING COMPUTER-READABLE CELL TRACKING PROGRAMS

CROSS-REFERENCE TO RELATED APPLICATIONS

This application is a Continuation Application of PCT Application No. PCT/JP2014/069558, filed Jul. 24, 2014 and based upon and claiming the benefit of priority from the prior Japanese Patent Application No. 2013-161531, filed Aug. 2, 2013, the entire contents of which are incorporated herein by reference.

BACKGROUND OF THE INVENTION

1. Field of the Invention

The present invention relates to a cell tracking device and a method for tracking a biological sample such as a cell on the basis of images of a cell image group collected using a microscope and measuring a displacement of the position of the biological sample, and a storage medium non-transitory storing computer-readable cell tracking programs.

2. Description of the Related Art

In researches in the fields of biology and medicine, for example, fluorescence and bioluminescence intensities which represent biological activity of a biological sample such as a living cell are observed, a biological sample and a bio-related substance to be examined are imaged, and variations in shape characteristics and of expression levels inside and outside the biological sample are chronologically observed. In this observation, the amount of light emitted from each individual living cell is chronologically measured in order to capture an expression level of a light-emitting gene as time passes. In the chronological measurement of the amount of light emission, time-lapse (very slow speed) imaging is performed to capture a dynamic functional expression of protein molecules in a biological sample such as a cell. This time-lapse imaging allows a time-lapse image sequence in which a plurality of time-lapse images are arranged in time series.

In measuring an amount of light emission chronologically, generally, the position of a biological sample such as a cell is visually confirmed from each image of the time-lapse image sequence, and the brightness value on the position or the average brightness within a predetermined region with the position at the center thereof or the like is plotted as an amount of light emitted from a cell.

However, the visual measurement is a very complicated operation. It is thus desirable to perform an automatic operation by a cell tracking process capable of continuing tracking a cell position with accuracy, to which an image recognition technology is applied.

For example, Jpn. Pat. Appln. KOKAI Publication No. 2010-14964 discloses a technology corresponding to the foregoing technology of measuring a displacement of a biological sample such as a cell. The publication discloses a biological observation device that allows image pickup for detection and image pickup for observation to be performed by a single image pickup device. The biological observation device includes an objective lens disposed close to a sample, an image acquisition unit which picks up the sample through the objective lens, an objective lens driving unit which drives the objective lens in a direction to correct a displacement of the sample, and a control unit which controls the image acquisition unit to capture an observing image for observing the sample and a detecting image for detecting a displacement of the sample. The biological observation device captures the observing image by long-time exposure and captures the detecting image by short-time exposure. The biological observation device uses an image with a small subject blur which is picked up by short-time exposure in order to detect a displacement of a sample.

BRIEF SUMMARY OF THE INVENTION

According to an aspect of the present invention, there is provided a cell tracking device including a first image acquisition unit configured to pick up images of a cell under a short-time exposure condition at a plurality of points in time to capture a plurality of short-time exposure images, a second image acquisition unit configured to pick up images of the cell under a long-time exposure condition to capture long-time exposure images, each image of the cell under the long-time exposure condition being picked up within each interval between the plurality of points in time, a first tracking unit configured to track the cell based upon the short-time exposure images, a second tracking unit configured to track the cell based upon the long-time exposure images, and an interpolation unit configured to interpolate a tracking result obtained by the second tracking unit with a tracking result obtained by the first tracking unit.

According to another aspect of the present invention, there is provided a cell tracking method including picking up images of a cell under a short-time exposure condition at a plurality of points in time to capture a plurality of short-time exposure images, picking up images of the cell under a long-time exposure condition to capture long-time exposure images, each image of the cell under the long-time exposure condition being picked up within each interval between the plurality of points in time, tracking the cell based upon the short-time exposure images, tracking the cell based upon the long-time exposure images, and interpolating a tracking result based upon the long-time exposure images with a tracking result based upon the short-time exposure image.

According to another aspect of the present invention, there is provided a storage medium non-transitory storing computer-readable cell tracking programs which are readable by a computer, the computer performing a first image pickup function for picking up images of a cell under a short-time exposure condition at a plurality of points in time to capture a plurality of short-time exposure images, a second image pickup function for picking up images of the cell under a long-time exposure condition to capture long-time exposure images, each image of the cell under the long-time exposure condition being picked up within each interval between the plurality of points in time, a first tracking function for tracking the cell based upon the short-time exposure images, a second tracking function for tracking the cell based upon the long-time exposure images, and an interpolation function for interpolating a tracking result obtained by the second tracking function with a tracking result obtained by the first tracking function.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a chart showing an example of timing with which a phase contrast image Pi(n) and a bioluminescence image Li(n) are captured by the device.

FIG. 4 is a cell tracking process flowchart in the device.

FIG. 5 is a diagram showing a cell tracking device according to a second embodiment.

DETAILED DESCRIPTION OF THE INVENTION

[First Embodiment]

A cell tracking device according to a first embodiment will be described below with reference to the drawings.

Figure 1:
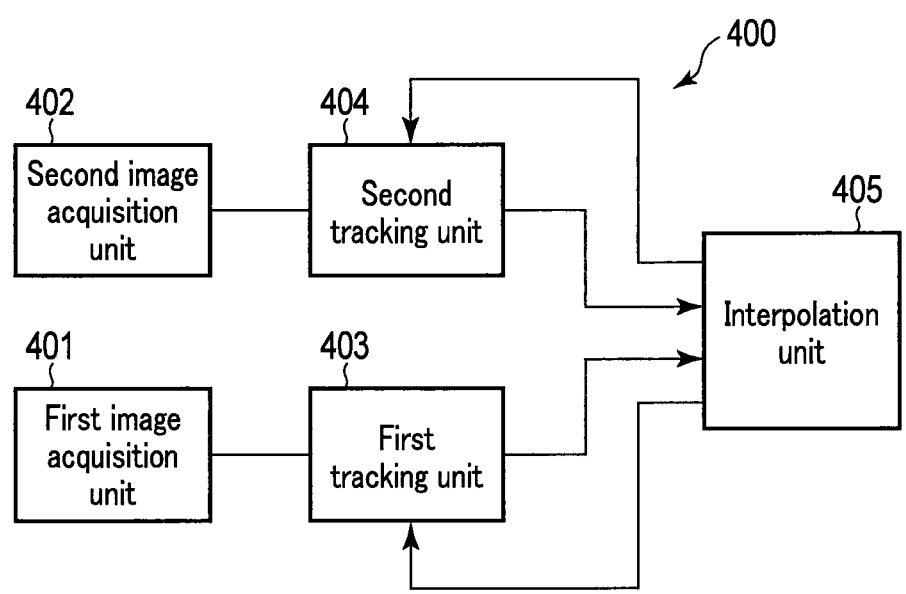
FIG. 1 is a block diagram showing a cell tracking device according to a first embodiment.

FIG. 1 is a block diagram of a cell tracking device (referred to as the present device 400 hereinafter). The present device 400 includes a first image acquisition unit 401, a second image acquisition unit 402, a first tracking unit 403, a second tracking unit 404 and an interpolation unit 405. The first image acquisition unit 401 picks up images of a cell under a short-time exposure condition at a plurality of points in time to capture a plurality of short-time exposure images. The second image acquisition unit 402 picks up an image of the cell under a long-time exposure condition within each interval between the points in time. The first tracking unit 403 tracks the cell on the basis of the short-time exposure images captured by the first image acquisition unit 401. The second tracking unit 404 tracks the cell on the basis of the long-time exposure images captured by the second image acquisition unit 402, together with the first tracking unit 403. The interpolation unit 405 interpolates a tracking result obtained by the second tracking unit 404 with a tracking result obtained by the first tracking unit 403.

The short-time exposure condition is a condition for capturing an image to detect a displacement of a cell.

The long-time exposure condition is a condition for capturing an image to observe a cell.

The present device 400 picks up images of a cell under a short-time exposure condition at a plurality of points in time by the first image acquisition unit 401 to capture a plurality of short-time exposure images, picks up an image of the cell under a long-time exposure condition within each interval between the points in time by the second image acquisition unit 402, tracks the cell on the basis of the short-time exposure images by the first tracking unit 403, tracks the cell on the basis of the long-time exposure images by the second tracking unit 404, and interpolates a tracking result obtained by the second tracking unit 404 with a tracking result obtained by the first tracking unit 403.

The first image acquisition unit 401 and the second image acquisition unit 402 pick up a cell image by different microscopic methods using, for example, a bioluminescence microscope and a phase contrast microscope. The first image acquisition unit 401 includes, for example, a phase contrast microscope or a differential interference contrast (DIC) microscope. The first image acquisition unit 401 captures a phase contrast image as a short-time exposure image using, for example, the phase contrast microscope. The second image acquisition unit 402 includes, for example, a bioluminescence microscope or a fluorescence microscope. The second image acquisition unit 402 captures a bioluminescence image as a long-time exposure image using, for example, the bioluminescence microscope.

The interpolation unit 405 tracks the cell using the second tracking unit 404 if the brightness value of a to-be-tracked target in the long-time exposure image captured by the second image acquisition unit 402 is equal to or larger than a predetermined threshold value. The interpolation unit 405 selects tracking of the cell using the first tracking unit 403 if the brightness value of the to-be-tracked target is smaller than the predetermined threshold value.

More specifically, the interpolation unit 405 compares the brightness average value of the surroundings of the to-be-tracked target in the long-time exposure image with a predetermined threshold value. If the brightness average value is equal to or larger than the predetermined threshold value, the interpolation unit 405 tracks the cell using the second tracking unit 404. If the brightness average value is smaller than the predetermined threshold value, the interpolation unit 405 selects tracking of the cell using the first tracking unit 403.

Figure 2:
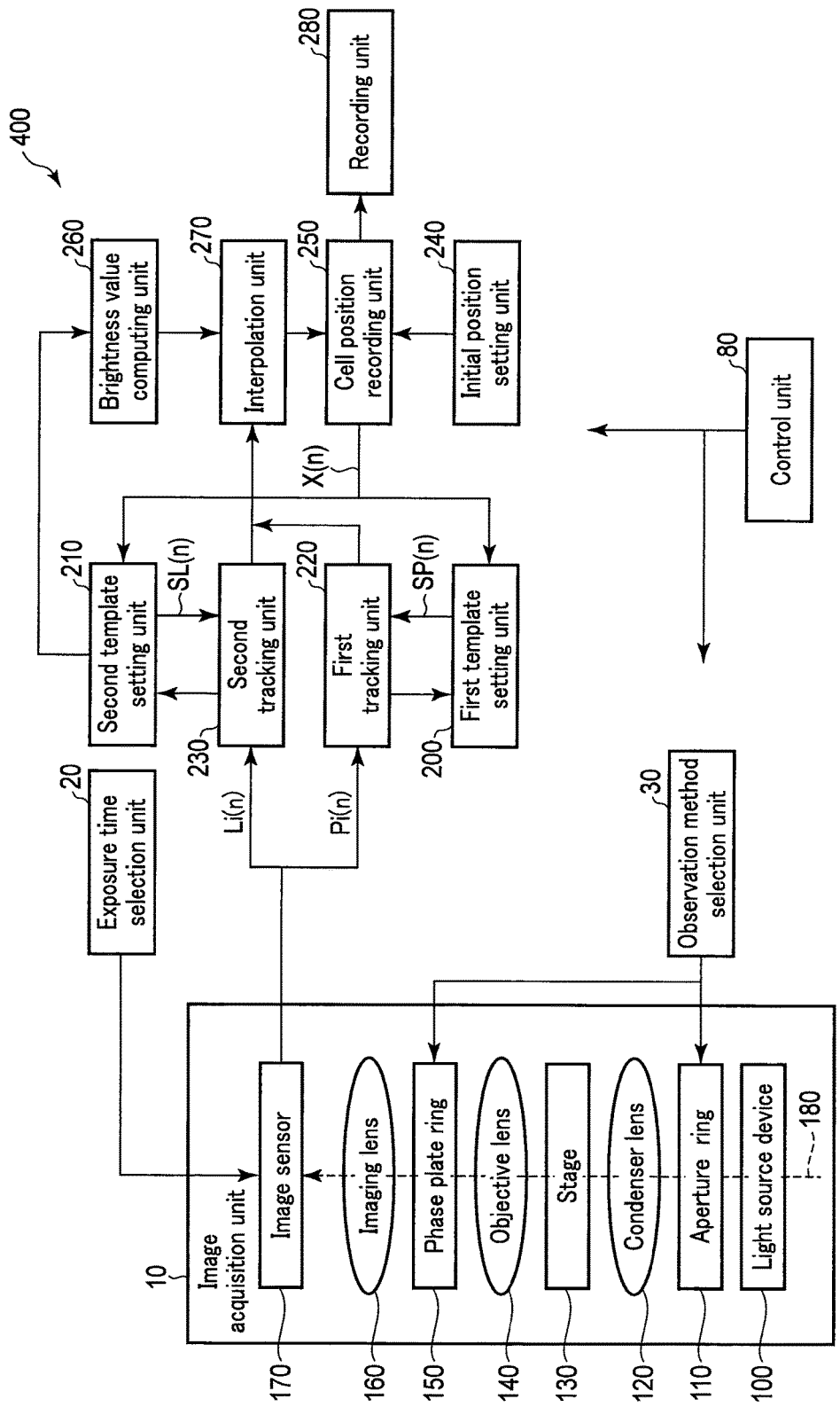
FIG. 2 is a diagram showing a specific example of the device.

FIG. 2 shows an example of a specific configuration of the present device 400. The present device 400 includes an image acquisition unit 10, an exposure time selection unit 20, an observation method selection unit 30, a first template setting unit 200, a second template setting unit 210, a first tracking unit 220, a second tracking unit 230, an initial position setting unit 240, a cell position recording unit 250, a brightness value computation unit 260, an interpolation unit 270, a recording unit 280 and a control unit 80.

The image acquisition unit 10 picks up an image of a cell placed on a stage 130 by time lapse (very slow speed) imaging at each of a plurality of points in time. The image acquisition unit 10 includes the first image acquisition unit 401 and the second image acquisition unit 402 shown in FIG. 1. The image acquisition unit 10 selects one of a plurality of microscopic methods with arbitrary timing to capture an image corresponding to the selected one of the microscopic methods. For example, the image acquisition unit 10 selects a phase contrast microscopic method for capturing a phase contrast image as a short-time exposure image or a bioluminescence microscopic method for capturing a bioluminescence image as a long-time exposure image. The image acquisition unit 10 picks up an image of a cell and selects the phase contrast microscopic method to capture a phase contrast image of the cell. The image acquisition unit 10 picks up an image of the cell and selects the bioluminescence microscopic method to capture a bioluminescence image of the cell.

In the image acquisition unit 10, a light source device 100, a condenser lens 120, the stage 130, an objective lens 140, a phase plate ring 150, an imaging lens 160 and an image sensor 170 are arranged in sequence on an optical axis 180.

The aperture ring 110 and the phase plate ring 150 are instruments necessary for capturing a phase contrast image by image pickup when the phase contrast microscopic method is selected. The aperture ring 110 and phase plate ring 150 are connected to the observation method selection unit 30, which will be described later, and are arranged on the optical axis 180 when the phase contrast microscopic method is selected by the observation method selection unit 30. The aperture ring 110 and the phase plate ring 150 are not always essential structural elements because they need not be arranged on the optical axis 180 when a phase contrast image is not captured as a short-time exposure image, such as when a differential interference contrast image is captured.

The image sensor 170 converts an enlarged image of a cell on the stage 130, which is formed on the image pickup surface, into an electrical signal. The image sensor 170 picks up an image as a short-time exposure image if the image acquisition unit 10 employs the phase contrast microscopic method. The image sensor 170 picks up an image as a long-time exposure image if the image acquisition unit 10 employs the bioluminescence microscopic method. The image sensor 170 includes an A/D converter to convert the electrical signal of the enlarged image of the cell digitally and output the digital image signal.

The image acquisition unit 10 is provided with the exposure time selection unit 20 and the observation method selection unit 30 to select one of the phase contrast microscopic method and the bioluminescence microscopic method for the image acquisition unit 10. The image acquisition unit 10 may be used to select one of the phase contrast microscopic method and the bioluminescence microscopic method.

For the image acquisition unit 10, the observation method selection unit 30 selects a phase contrast microscopic method for capturing a phase contrast image as a short-time exposure image or a bioluminescence microscopic method for capturing a bioluminescence image as a long-time exposure image. The observation method selection unit 30 issues an instruction to attach and detach the aperture ring 110 and the phase plate ring 150 to and from the optical axis 180. More specifically, the observation method selection unit 30 issues an instruction to attach the aperture ring 110 and the phase plate ring 150 onto the optical axis 180 at the same time only when a phase contrast image of a cell is picked up by the phase contrast microscopic method. The observation method selection unit 30 issues an instruction to detach the aperture ring 110 and the phase plate ring 150 from the optical axis 180 when a bioluminescence image of a cell is picked up by the bioluminescence microscopic method.

The exposure time selection unit 20 provides the image sensor 170 with an instruction to set the exposure time to the short-time exposure condition when an image is picked up by the short-time exposure microscopic method. The short-time exposure condition is, for example, exposure time Pt of a few seconds or shorter, such as exposure time Pt=1.0 sec.

The exposure time selection unit 20 provides the image sensor 170 with an instruction to set the exposure time to the long-time exposure condition when an image is picked up by the long-time exposure microscopic method. The long-time exposure condition is, for example, exposure time Lt of several tens of minutes, such as exposure time Lt=3600 sec.

The image sensor 170 is connected to the first tracking unit 220 corresponding to the first tracking unit 403 shown in FIG. 1 and the second tracking unit 230 corresponding to the second tracking unit 404 shown in FIG. 1. The first tracking unit 403 includes the first tracking unit 220 and the first template setting unit 200. The second tracking unit 404 includes the second tracking unit 230 and the second template setting unit 210.

In the first template setting unit 200, a first template image is recorded to track a cell using phase contrast images as short-time exposure images by the first tracking unit 220.

In the second template setting unit 210, a second template image is recorded to track a cell using bioluminescence images as long-time exposure images by the second tracking unit 230.

The first tracking unit 220 and the first template setting unit 200 are connected to each other to allow data communications between them. The first tracking unit 220 tracks a cell on the phase contrast images as the short-time exposure images by the template matching method using the first template image recorded in the first template setting unit 200.

The second tracking unit 230 and the second template setting unit 210 are connected to each other to allow data communications between them. The second tracking unit 230 tracks a cell on the bioluminescence images as the long-time exposure images by the template matching method using the second template image recorded in the second template setting unit 210.

The case where the first tracking unit 220 and the second tracking unit 230 each use the template matching has been described; however, in order to track a cell by each of the first and second tracking units 220 and 230, not only the template matching but also, for example, a tracking method using a particle filter and a tracking method using a mean shift method may be used.

The first tracking unit 220 and the second tracking unit 230 are each connected to the interpolation unit 270 corresponding to the interpolation unit 405 shown in FIG. 1. The second template setting unit 210 is connected to the interpolation unit 270 through the brightness value computation unit 260. The interpolation unit 270 is connected to the cell position recording unit 250. The initial position setting unit 240 is connected to the cell position recording unit 250. The cell position recording unit 250 is connected to the first template setting unit 200, the second template setting unit 210 and the recording unit 280.

The brightness value computation unit 260 captures a second template image recorded in the setting template setting unit 210 and computes a brightness average value of all pixels included in the second template image. In this computation, the brightness average value Lum(n−1) computed by the brightness value computation unit 260 is used. Instead, an amount of variation in the brightness value, a standard deviation or brightness gradient of the brightness value, or an edge amount can be used.

When a user designates the initial position coordinate of a cell to be tracked in the pick-up image, the initial position setting unit 240 transfers the initial position coordinate to the cell position recording unit 250.

The cell position recording unit 250 receives the initial position coordinate transferred from the initial position setting unit 240, records this initial position coordinate in the recording unit 280 as a cell position in, for example, a first frame, and transfers this cell position to each of the first and second template setting units 200 and 210.

The interpolation unit 270 interpolates a tracking result obtained by the second tracking unit 230 with a tracking result obtained by the first tracking unit 220. The interpolation unit 270 and, for example, the cell position recording unit 250 correspond to the interpolation unit 405 shown in FIG. 1.

If the brightness value of all pixels included in the second template image is equal to or larger than a predetermined threshold value, the interpolation unit 270 transfers the cell position in the cell position recording unit 250 to the second tracking unit 230 to track a cell. If the brightness value is smaller than the predetermined threshold value, the interpolation unit 270 transfers the cell position in the cell position recording unit 250 to the first tracking unit 220 to select the cell tracking of the first tracking unit 220.

The control unit 80 is a system controller that is connected to the foregoing units of the present device 400 to centralize control of the respective units. The control unit 80 executes the programs of the cell tracking process flowchart shown in FIG. 4, which will be described later. The control unit 80 may be implemented by a computer including a memory for non-transitory storing the programs and a microprocessor for executing the programs. Each or all of the foregoing units 20, 30, 200, 210, 220, 230, 240, 250, 260 and 270 may be implemented by hardware circuitry or by a computer including a microprocessor and a memory for non-transitory storing programs which operation of each unit is made to perform to the microprocessor.

Next, a detailed configuration for performing a tracking process in the present device 400 will be described.

A cell to be observed is put in a given container and the container is placed on the stage 130. The cell is, for example, a luminescent sample and specifically a luminescent cell introducing a luciferase gene is used.

The image acquisition unit 10 includes the light source device 100. The light source device 100 irradiates a cell with illumination light when a phase contrast image is captured by the phase contrast microscopic method. This light source device 100 is applied to a speculum method for capturing a phase contrast image, a differential interference contrast image, a bioluminescence image or a fluorescent image by the image acquisition unit 10. As the light source device 100, for example, a mercury lamp, a halogen lamp, or a xenon lamp is used.

The condenser lens 120 condenses the illumination light output from the light source device 100.

The objective lens 140 and the imaging lens 160 enlarge an image of a cell and the enlarged image is formed on the image pickup surface of the image sensor 170.

The aperture ring 110 and phase plate ring 150 are arranged on the optical axis 180 of the image acquisition unit 10 when a phase contrast image is captured by the phase contrast microscopic method. Thus, the aperture ring 110 and phase plate ring 150 shift a phase of the illumination light output from the light source device 100 to make a phase contrast.

The image sensor 170 converts the enlarged image of the cell formed on the image pickup surface into an electrical signal. This image sensor 170 includes an A/D converter to convert the electrical signal of the enlarged image of the cell digitally and output the digital image signal.

The exposure time selection unit 20 provides the image sensor 170 with an instruction to set the exposure time to the short-time exposure condition (exposure time Pt of a few seconds or shorter, such as exposure time Pt=1.0 sec) when an image is picked up by the short-time exposure microscopic method.

The exposure time selection unit 20 provides the image sensor 170 with an instruction to set the exposure time to the long-time exposure condition (exposure time Lt of several tens of minutes, such as exposure time Lt=3600 sec) when an image is picked up by the long-time exposure microscopic method.

The observation method selection unit 30 issues an instruction to attach and detach the aperture ring 110 and the phase plate ring 150 to and from the optical axis 180. For example, the observation method selection unit 30 issues an instruction to attach the aperture ring 110 and the phase plate ring 150 onto the optical axis 180 at the same time only when a phase contrast image of a cell is picked up by the phase contrast microscopic method.

Furthermore, the observation method selection unit 30 issues an instruction to detach the aperture ring 110 and the phase plate ring 150 from the optical axis 180 when a bioluminescence image of a cell is picked up by the bioluminescence microscopic method.

In the present device 400, a plurality of cell images are picked up and collected in time series by image pickup of the image acquisition unit 10, thus capturing a cell image group including the cell images. This cell image group includes a plurality of cell images which are picked up and collected by picking up images of a cell to be observed at a plurality of points in time for each predetermined image pickup period.

The image pickup of the image acquisition unit 10 is performed by selecting an exposure condition (short-time exposure and long-time exposure) and a microscopic method (e.g., a phase contrast microscopic method and a bioluminescence microscopic method) for each image pickup in response to each of the instructions from the observation method selection unit 30 and the exposure time selection unit 20. In other words, as described above, the image acquisition unit 10 includes the first image acquisition unit 401 and the second image acquisition unit 402 which are selected in response to each of the instructions from the observation method selection unit 30 and the exposure time selection unit 20. The first image acquisition unit 401 picks up images of a cell under the short-time exposure condition at a plurality of points in time to capture a plurality of short-time exposure images. The second image acquisition unit 402 picks up an image of a cell under the long-time exposure condition within each interval between the points in time to capture a long-time exposure image.

If T is a predetermined point in time, I is a time interval and N is an integer of 0 or more, the first image acquisition unit 401 picks up images of a cell under the short-time exposure condition at a plurality of points in time T+N×I.

The second image acquisition unit 402 picks up images of a cell under the long-time exposure condition within a plurality of intervals T+N×I to T+(N+1)×I.

The first image acquisition unit 401 and the second image acquisition unit 402 pick up images of a cell by observation methods of different microscopic methods. If the exposure condition is short-time exposure, the phase contrast microscopic method is selected as the microscopic method. If the exposure condition is long-time exposure, the bioluminescence microscopic method is used as the microscopic method.

Hereinafter, a short-time exposure cell image picked up at the n-th time by the short-time exposure microscopic method will be described as Pi(n) and a long-time exposure cell image picked up at the n-th time by the long-time exposure microscopic method will be described as Li(n), wherein n is a natural number of 1, 2, 3, . . . .

Assume that the phase contrast image Pi(n) and the bioluminescence image Li(n) are alternately picked up and captured by the image acquisition unit 10, as follows: Pi(1), Li(1), Pi(2), Li(2), . . . , Pi(n), Li(n), Pi(n+1), Li(n+1), . . . .

FIG. 3 shows an example of timing with which a phase contrast image Pi(n) and a bioluminescence image Li(n) are captured. In FIG. 3, for example, a bioluminescence image Li(n−1), a phase contrast image Pi(n), a bioluminescence image Li(n) and a phase contrast image Pi(n+1) are captured in that sequence.

If a first image pickup start point in the phase contrast microscopic method is TS, the long-time exposure time is TL and the short-time exposure time is TP, the image pickup start point of the phase contrast image Pi(n) is expressed by:

$$TS+(n-1)(TP+TL) \quad (1)$$

The image pickup start point of the bioluminescence image Li(n) is expressed by:

$$TS+(n-1)(TP+TL)+TP \quad (2)$$

Furthermore, if the short-time exposure time TP is considerably shorter than the long-time exposure time TL, the image pickup points in time of the phase contrast image Pi(n) and the bioluminescence image Li(n) can be considered to be approximately the same, or they can be expressed by TS+TL(n−1).

In the image pickup using the phase contrast microscopic method, the aperture ring 110 and the phase plate ring 150 are attached onto the optical axis 180 of the image acquisition unit 10 in response to an instruction from the observation method selection unit 30, and the exposure time is set to the short-time exposure condition (exposure time Pt=1.0 sec) in response to an instruction from the exposure time selection unit 20.

The phase contrast microscopic method is a microscopic method using a light diffraction phenomenon. The phase contrast microscopic method is suitable for observing an object such as a transparent cell and microbe because a phase difference of light (optical path difference) which passes through substances having different refractive indices, can be obtained as contrast.

The phase contrast microscopic method has the feature of presenting a great contrast, which is called a halo (artifact), on the boundary between a background region and a cell. This halo appears as aura-like light chiefly on a boundary portion between a background region and each individual cell region in a cell image. The phase contrast microscopic method having this feature makes it possible to capture a clear image with no blur under the short-time exposure image pickup condition.

In place of the phase contrast microscopic method, a bright field microscope such as a differential interference contrast microscope having a similar image quality characteristic, may naturally be employed.

When the phase contrast macroscopic method is selected, the phase contrast short-time exposure image Pi(n) picked up by the image acquisition unit 10 is transferred to the first tracking unit 220.

In the image pickup using the bioluminescence microscopic method, the aperture ring 110 and the phase plate ring 150 are detached from the optical axis 180 of the image acquisition unit 10 in response to an instruction from the observation method selection unit 30, and the exposure time in the image sensor 170 is set to the long-time exposure condition (exposure time Lt of several tens of minutes, such as exposure time Lt=3600 sec) in response to an instruction from the exposure time selection unit 20.

The imaging using the bioluminescence microscopic method needs to be performed under the long-time exposure condition and using a cooled CCD or a bright optical system because a weak light due to photoprotein that appears from a luminescent cell introducing a luciferase gene is caught at high sensitivity. Unlike the fluorescence microscope, the bioluminescence microscopic method needs no excitation light for detection; thus, a bioluminescence image can be captured without causing damage to a cell.

In place of the bioluminescence microscopic method, a fluorescence microscopic method may be employed. In order to avoid damage to a cell and color fading of a fluorescent sample even in fluorescence imaging, weak-excitation and long-time exposure may be performed at low laser sensitivity. In this case, an image having a quality characteristic similar to that of an image captured by the bioluminescence microscope is picked up.

When the bioluminescence macroscopic method is selected, the bioluminescence long-time exposure image Li(n) picked up by the image acquisition unit 10 is transferred to the second tracking unit 230.

Next, a process of a first frame (n=1) immediately after the start of image pickup will be described.

In the first-frame process, a process for tracking a cell is not performed but the initial position of a cell to be tracked is only set, because there is no old frame image.

In setting the initial position of a cell, first, a first-frame phase contrast image Pi(1) picked up by the image acquisition unit 10 is transferred to the first template setting unit 200 via the first tracking unit 220. Along with this, a first-frame bioluminescence image Li(1) is transferred to the second template setting unit 210 via the second tracking unit 230. At this time, neither the first tracking unit 220 nor the second tracking unit 230 performs a process of tracking a cell.

Next, when a user designates the initial position coordinate X(n)=x(1) of a cell to be tracked in a pickup image, the initial position setting unit 240 transfers the initial position coordinate x(1) to the cell position recording unit 250. The sign x in the initial position coordinate x(1) is position vector x(x1,x2). The signs x1 and x2 respectively represent an X (horizontal) coordinate and a Y (vertical) coordinate in the cell image. The position coordinate of a cell may be automatically detected using a known region segmentation process (e.g., a watershed method, a level set method, and a graph cut method), and the position coordinate may automatically be designated as the initial position coordinate x(1).

The cell position recording unit 250 receives the initial position coordinate x(1) from the initial position setting unit 240, records the initial position coordinate x(1) in the first frame as a cell position, and transfers the cell position to the first template setting unit 200 and the second template setting unit 210.

The first template setting unit 200 receives the initial position coordinate x(1) from the cell position recording unit 250 and extracts from the phase contrast image Pi(1) an image in a rectangular region (template region) of a predetermined size with the initial position coordinate x(1) at its center, as a first template image SP(1). This extraction is performed by the template matching process described later. The first template setting unit 200 temporarily records the extracted first template image SP(1) in a recording medium, such as a built-in image buffer, a RAM and an external memory.

The second template setting unit 210 receives the initial position coordinate x(1) from the cell position recording unit 250 and extracts from the bioluminescence image Li(1) an image in the rectangular region (template region) of a predetermined size with the initial position coordinate x(1) at its center, as a second template image SL(1). This extraction is performed by the template matching process described later. The second template setting unit 210 temporarily records the extracted second template image SL(1) as well as the first template image SP(1) in a recording medium, such as a built-in image buffer, a RAM and an external memory.

Next, an outline of a tracking process using a template matching process applied as a tracking method in the foregoing first tracking unit 220 and second tracking unit 230 will be described.

For example, to detect which position in the current frame image I(n) a cell to be tracked in the preceding frame image I(n−1) moves to, in the template matching method, a rectangular region of a predetermined size with the cell to be tracked at the center thereof in the preceding frame image I(n−1) is first set as a template region A(n−1).

Next, a rectangular region B(n, p) (p represents a pixel included in the current frame image I(n)) of the same size as that of the template region A(n−1) with a pixel at its center for each of the positions of all pixels in the current frame image I(n), is set. Then, a similarity between the template region A(n−1) and the rectangular region B(n, p) is measured. As the similarity, for example, a Sum of Squared Difference (SSD) is used.

As a result of measurement of the similarity between the template region A(n−1) and the rectangular region B(n, p), the position coordinate of pixel p of the rectangular region B(n, p) which is the most similar to (whose differences are smaller than those of) the template region A(n−1) is assumed as a position of a cell moved on the current frame image I(n).

Next, a process of the n-th frame (n>1) will be described.

The phase contrast image Pi(n) of the n-th frame picked up by the image acquisition unit 10 is transferred to the first tracking unit 220. The bioluminescence image Li(n) is transferred to the second tracking unit 230.

At this point in time, a first template image SP(n−1) set in advance at the time of processing of the preceding frame is recorded in the first template setting unit 200. Then, the first template image SP(n−1) is transferred to the first tracking unit 220.

A second template image SL(n−1) set in advance at the time of processing of the preceding frame is recorded in the second template setting unit 210. Then, the second template image SL(n−1) is transferred to the second tracking unit 230.

The first tracking unit 220 assumes a cell position coordinate xP(n) in the current frame from the phase contrast image Pi(n) and the first template image SP(n−1) by the foregoing template matching method. This cell position coordinate xP(n) is transferred to the interpolation unit 270.

The second tracking unit 230 assumes a cell position coordinate xL(n) in the current frame from the bioluminescence image Li(n) and the second template image SL(n−1) by the foregoing template matching method. This cell position coordinate xL(n) is also transferred to the interpolation unit 270.

Next, the brightness value computation unit 260 obtains a second template image SL(n−1) from the second template setting unit 210. The brightness value computation unit 260 computes the brightness average value Lum(n−1) of all the pixels included in the obtained second template image SL(n−1) and transfers the brightness average value Lum(n−1) to the interpolation unit 270.

The interpolation unit 270 interpolates a tracking result obtained by the second tracking unit 230 with a tracking result obtained by the first tracking unit 220. The interpolation unit 270 tracks a cell which is tracked by the second tracking unit 230 if the brightness value in a long-time exposure image captured by the second image acquisition unit 402 is equal to or larger than a predetermined threshold value. The interpolation unit 207 selects tracking of a cell which is tracked by the first tracking unit 220 if the brightness value is smaller than the predetermined threshold value.

The interpolation unit 270 receives the cell position coordinate xP(n) from the first tracking unit 220 and the cell position coordinate xL(n) from the second tracking unit 230, and also receives the brightness average value Lum(n−1) from the brightness value computation unit 260. The interpolation unit 270 compares the predetermined threshold value and the brightness average value Lum(n−1). As a result of the comparison, when the brightness average value Lum(n−1) is equal to or larger than the threshold value, the interpolation unit 270 specifies the cell position coordinate xL(n) of a tracking result (position coordinate) based upon the bioluminescence image i(n), as a cell position X(n) in the n-th frame image, with the cell having a predetermined bioluminescence intensity on the bioluminescence image Li(n). This cell position X(n) is transferred to the cell position recording unit 250.

When the brightness average value Lum(n−1) is smaller than the threshold value, the interpolation unit 270 tracks a cell on the basis of the phase contrast image Pi(n), while the cell has a low emission intensity on the bioluminescence image Li(n) and the tracking process decreases in its reliability. Then, the interpolation unit 270 specifies the cell position coordinate xP(n) of the tracking result (position coordinate) based upon the phase contrast image Pi(n), as a cell position X(n) in the n-th frame image, instead of the position coordinate xL(n) obtained from the bioluminescence image Li(n). This cell position X(n) is transferred to the cell position recording unit 250.

The cell position recording unit 250 records a cell position X(n) of the tracking result based upon the bioluminescence image i(n) in the n-th frame or a cell position X(n) of the tracking result based upon the phase contrast image Pi(n). The cell position recording unit 250 transfers the recorded cell position X(n) to the first template setting unit 200 and the second template setting unit 210.

The first template setting unit 200 receives the cell position X(n) from the cell position recording unit 250. The first template setting unit 200 extracts from the phase contrast image Pi(n) a rectangular region of a predetermined size with the cell position X(n) at its center, as a first template image SP(n) in the template matching process. The first template setting unit 200 temporarily records the extracted first template image SP(n) in a built-in image buffer.

The second template setting unit 210 receives the cell position X(n) from the cell position recording unit 250. The second template setting unit 210 extracts from the bioluminescence image Li(n) a rectangular region of a predetermined size with the cell position X(n) at its center, as a second template image SL(n) in the template matching process. The second template setting unit 210 temporarily records the extracted second template image SL(n) in the built-in image buffer.

When the image pickups of the image acquisition unit 10 are completed, each cell position X(n) (n=1 to the total number of frames) in all of the frame images recorded in the cell position recording unit 250 is transferred to the recording unit 280 and recorded on predetermined media.

Next, an example of a cell tracking process performed by the present device will be described in accordance with the flowchart for the cell tracking process shown in FIG. 4.

In step S10, the control unit 80 determines whether a first-frame image is picked up. If a first-frame image is picked up, the control unit 80 shifts to step S20. As a result of the determination, if not a first-frame image but a second-frame image or its subsequent-frame images are picked up, the control unit 80 shifts to step S70.

In step S20, the first tracking unit 220 receives a first-frame phase contrast image Pi(1) picked up under the short-time exposure condition.

In step S30, the second tracking unit 230 receives a first-frame bioluminescence image Li(1) picked up under the long-time exposure condition.

In step S40, when a user designates the initial position coordinate x(1) of a cell to be tracked in a picked-up image, the initial position setting unit 240 sets the initial position coordinate x(1).

In step S50, the first template setting unit 200 extracts a first template image SP(1) with a cell position at its center from the phase contrast image Pi(1) received from the first tracking unit 220, on the basis of the initial position coordinate x(1) set in the step S40, and records it temporarily in the built-in buffer.

In step S60, the second template setting unit 210 extracts a second template image SL(1) with a cell position at its center from the bioluminescence image Li(1) received from the second tracking unit 230, on the basis of the initial position coordinate x(1) set in the step S40, and records it temporarily in the built-in buffer.

In step S70, the first tracking unit 220 receives an n-th (n>1) frame phase contrast image pi(n).

In step S80, the second tracking unit 230 receives an n-th (n>1) frame bioluminescence image Li(n).

In step S90, the first tracking unit 220 assumes a cell position xP(n) on the n-th frame phase contrast image Pi(n) on the basis of the first template image SP(n−1) recorded in the first template setting unit 200 by the template matching method at the time of n−1 frame processing.

In step S100, the second tracking unit 230 assumes a cell position xL(n) on the n-th frame bioluminescence image Li(n) on the basis of the second template image SL(n−1) recorded in the second template setting unit 210 by the template matching method at the time of n−1 frame processing.

In step S110, the brightness value computation unit 260 computes an emission brightness average value Lum(n−1) of all pixels of the second template image SL(n−1) corresponding to the (n−1)-th frame bioluminescence image Li(n−1).

In step S120, the interpolation unit 270 receives a cell position coordinate xP(n) from the first tracking unit 220. Along with this, the interpolation unit 270 receives a cell position coordinate xL(n) from the second tracking unit 230 and receives a brightness average value Lum(n−1) from the brightness value computation unit 260.

The interpolation unit 270 compares a preset threshold value with the brightness average value Lum(n−1). When the brightness average value Lum(n−1) is equal to or larger than the threshold value as a result of the comparison, the interpolation unit 270 specifies the cell position coordinate xL(n) of a tracking result (position coordinate) based upon the bioluminescence image i(n) as a cell position X(n) in the n-th frame image, while the cell has a predetermined emission intensity on the bioluminescence image Li(n).

When the brightness average value Lum(n−1) is smaller than the threshold value, in step S120, the interpolation unit 270 tracks a cell on the basis of the phase contrast image Pi(n), while the cell has a low emission intensity on the bioluminescence image Li(n) and the tracking process decreases in its reliability. Then, the interpolation unit 270 specifies the cell position coordinate xP(n) of the tracking result (position coordinate) based upon the phase contrast image Pi(n), as a cell position X(n) in the n-th frame image, instead of the position coordinate xL(n) obtained from the bioluminescence image Li(n).

In step S130, the cell position recording unit 250 records the cell position X(n) of the tracking result based upon the n-th frame bioluminescence image i(n) or the cell position X(n) of the tracking result based upon the phase contrast image Pi(n).

In step S140, the first template setting unit 200 extracts a first template image SP(n) with a cell position at its center from the phase contrast image Pi(n) received from the first tracking unit 220 on the basis of the cell position X(n) recorded in the step S130, and temporarily records it in the built-in buffer.

In step S150, the second template setting unit 210 extracts a second template image SL(n) with a cell position at its center from the bioluminescence image Li(n) received from the second tracking unit 230 on the basis of the cell position X(n) recorded in the step S130, and temporarily records it in the built-in buffer.

In step S160, the control unit 80 shifts to above step S70 when there is a next frame image and it shifts to step S170 when there is no subsequent frame image.

In step S170, the control unit 80 records the cell positions X(n) in all of the frame images on predetermined media, and completes the process. This cell positions X(n) are transferred to, for example, the recording unit 280 and recorded on predetermined media.

According to the first embodiment described above, the brightness average value Lum(n−1) of the bioluminescence image Li(n−1) and the preset threshold value are compared with each other and when the brightness average value Lum(n−1) of the bioluminescence image Li(n−1) is equal to or larger than the threshold value, the cell position X(n) of a tracking result based upon the bioluminescence image i(n) is specified with the cell having a predetermined emission intensity on the bioluminescence image Li(n), thus tracking a biological sample such as a cell. When the brightness average value Lum(n−1) of the bioluminescence image Li(n−1) is smaller than the threshold value, the cell has a low emission intensity on the bioluminescence image Li(n) and the tracking process is decreased in its reliability, with the result that the cell position X(n) of the tracking result based upon the phase contrast image Pi(n) is specified to track a biological sample such as a cell.

According to the first embodiment described above, a position variation of a biological sample such as a cell can be measured with high precision on the basis of a cell image group captured by the long-time exposure image pickup based upon the bioluminescence image Li(n) and the short-time exposure image pickup based upon the phase contrast image Pi(n), with the result that the biological sample can accurately be tracked. If the tracking is based upon the bioluminescence image i(n), it is unnecessary to radiate excitation light and it is possible to chronologically pick up a stable image whose spatial resolution is low but which can be used for quantitative evaluation. If the tracking is based upon the phase contrast image Pi(n), a phase difference of light (optical path difference) which passes through substances having different refractive indices, can be obtained as contrast; thus, the tracking is favorable for observing an object such as a transparent cell and microbe.

The background of researches in the fields of biology and medicine will be described. In these fields, a technology of detecting biological activity of a biological sample such as a living cell by a reporter assay is widely utilized. In the reporter assay, the gene of a cell whose activity is to be examined is replaced with a reporter gene involving fluorescence expression and bioluminescence (green fluorescence protein GFP, a luciferase gene, etc.), and fluorescence and emission intensities representing the biological activity are observed to visualize the cell, for example, to image a biological sample and a bio-related substance to be examined. It is thus possible to chronologically observe variations in shape characteristics and of expression levels inside and outside the biological sample. More specifically, in the field of research utilizing observation using fluorescence and bioluminescence as a reporter substance, time-lapse (very slow speed) imaging is performed to capture a dynamic functional expression of protein molecules in a sample.

The time-lapse imaging of a fluorescent sample has the properties of decreasing the amount of light emitted from the fluorescent sample by continuing irradiation of excitation light as time passes. Thus, in the time-lapse imaging, it is possible to pick up a clear image with a high spatial resolution for a short exposure time but is difficult to chronologically pick up a stable image which can be used for quantitative evaluation.

In chronological observation of a dynamic variation due to a time lapse directed to a luminescent sample, unlike in image pickup using fluorescence, excitation light need not be radiated, and a stable image whose spatial resolution is low but which can be used for quantitative evaluation can be picked up chronologically. In the chronological observation, therefore, the amount of light emitted from the luminescent sample is measured and the shape of the sample is observed. Since, however, the light emission of each cell is weak, in the chronological observation of a dynamic variation, an image of the cell is picked up using a bright optical system such as a CCD camera, long-time exposure and the like.

The luminescent sample is produced by introducing a light-emitting gene (luciferase gene) in a cell. As a method for introducing a light-emitting gene, for example, electroporation in which an electric pulse is applied to cells is used. In observing a cell into which a luciferase gene is introduced, the shape of the cell is examined from the intensity of expression (specifically, expression level) of the luciferase gene and the distribution of expression levels. Thus, the amount of light emitted from a cell due to luciferase activity is measured.

In order to capture the emission level of a light-emitting gene as time passes, the amount of light emitted from each individual living cell is measured chronologically. In the measurement, generally, a cell position is visually confirmed from each image of a time-lapse image sequence of a cell and, for example, the average brightness within a predetermined region with the cell position at the center thereof is plotted as an amount of light emitted from the cell. However, the visual measurement is a very complicated operation and thus it is desired to automatically perform an operation by a cell tracking process capable of continuing tracking the cell position with accuracy.

When an image of a luminescent sample is picked up, the amount of light emitted from the sample is very small and thus it needs to be picked up by long-time exposure. In the long-time exposure image pickup, it is more difficult to capture a clear image than in fluorescence image pickup and the like. Furthermore, in the long-time exposure image pickup, a generally-called motion blur which reflects the motion of a cell of an object by long-time exposure image pickup, is caused, and a stable, clear bioluminescence image is difficult to pick up. Accordingly, a high-precision cell tracking process for the bioluminescence images is more difficult to achieve than a process based upon a general fluorescent image.

In contrast, according to the first embodiment, a position variation of a living sample such as a cell can be measured with high precision on the basis of a group of cell images captured by the long-time exposure image pickup based upon the bioluminescence image $Li(n)$ and the short-time exposure image pickup based upon the phase contrast image $Pi(n)$ as described above, and the living sample can correctly be tracked.

[Second Embodiment]

Next, a second embodiment will be described with reference to the drawings. The components of the second embodiment, which are the same as those of the first embodiment, are denoted by the same reference numerals and their detailed descriptions are omitted.

The second image acquisition unit 402 in the present device 400 shown in FIG. 1 picks up images of a cell under a short-time exposure condition during an interval including periods before and after a plurality of points in time to capture a plurality of short-time exposure images, and compose the short-time exposure images, thereby falsely creating an image corresponding to a long-time exposure image captured by picking up an image of a cell under the long-time exposure condition during an interval including periods before and after each of a plurality of points in time.

The second tracking unit 404 tracks the cell on the basis of the long-time exposure image corresponding to the image falsely created by the second image acquisition unit.

Assume here that T is a predetermined point in time, I is a time interval and N is an integer of 0 or more.

The second image acquisition unit 402 captures a plurality of short-time exposure images by picking up images of a cell under the short-time exposure condition at a plurality of points in time during a plurality of intervals $T+N \times I-(I/2)$ to $T+N \times I+(I/2)$ including periods before and after a plurality of points in time $T+N \times I$.

The second image acquisition unit 402 falsely creates an image corresponding to a long-time exposure image captured by picking up an image of a cell under the long-time exposure condition during each of the intervals $T+N \times I-(I/2)$ to $T+N \times I+(I/2)$.

FIG. 5 is a block diagram specifically showing an image processing apparatus. The present device 400 excludes the exposure time selection unit 20 and the observation method selection unit 30 in the first embodiment and newly includes an exposure time selection unit 300, an observation method selection unit 310 and an bioluminescence pseudo-long-time exposure image creation unit 320. The exposure time selection unit 300 and the observation method selection unit 310 are respectively substituted for the exposure time selection unit 20 and the observation method selection unit 30 in the first embodiment.

The image sensor 170 is connected to the bioluminescence pseudo-long-time exposure image creation unit 320. The bioluminescence pseudo-long-time exposure image creation unit 320 is connected to the second tracking unit 230. The bioluminescence pseudo-long-time exposure image creation unit 320 composes a plurality of short-time exposure images to falsely create an image corresponding to a long-time exposure image captured by picking up an image of a cell under the long-time exposure condition during an interval including periods before and after each of a plurality of points in time.

Like in the foregoing first embodiment, the image pickup of the image acquisition unit 10 is performed by selecting an exposure condition (short-time exposure or long-time exposure) and a microscopic method (a phase contrast microscopic method or a bioluminescence microscopic method)

for each image pickup in response to each of the instructions from the observation method selection unit 310 and the exposure time selection unit 300.

The foregoing first embodiment is based upon the premise that the image pickup points in time of the phase contrast image Pi(n) and the bioluminescence image Li(n) are almost the same and there is no large displacement between them in the position of a cell to be tracked. In this first embodiment, it is compared whether the brightness average value Lum (n−1) of the bioluminescence image Li(n−1) is larger or smaller than the threshold value and in accordance with a result of this comparison, a living sample such as a cell is tracked on the basis of the bioluminescence image Li(n) or the phase contrast image Pi(n). However, the exposure time of the phase contrast image Pi(n) is shorter than 1 sec and the exposure time of the bioluminescence image Li(n) is under 60 min and thus there is a very wide difference between them. If, therefore, the image pickup point in time is considered to be the midpoint from the beginning of the exposure time to the end thereof, a very wide difference will be caused in the image pickup point in time between the phase contrast image Pi(n) and the bioluminescence image Li(n) and the cell position will be varied.

In the second embodiment, a plurality of short-time exposure images are captured by picking up images of a cell under a short-time exposure condition during an interval including periods before and after each of a plurality of points in time. In other words, in the second embodiment, in order to capture a bioluminescence image Li(n), a plurality of bioluminescence images Li(n) are picked up by short exposure at a plurality of points in time in each interval before and after an image pickup point in time of the phase contrast image Pi(n) as a reference. Then, the plurality of bioluminescence images Li(n) are composed into a bioluminescence image Li(n) whose image pickup point in time falsely coincides with that of the phase contrast image Pi(n), and the bioluminescence image Li(n) is used for a tracking process.

In this second embodiment, the image acquisition unit 10 picks up M bioluminescence images Li1(n,m) and Li2(n,m) at a plurality of points in time in each interval "before" and "after" the image pickup point in time of the phase contrast image Pi(n) under the control of the exposure time selection unit 300 and the observation method selection unit 310, where m is equal to 1 to M.

Figure 6:
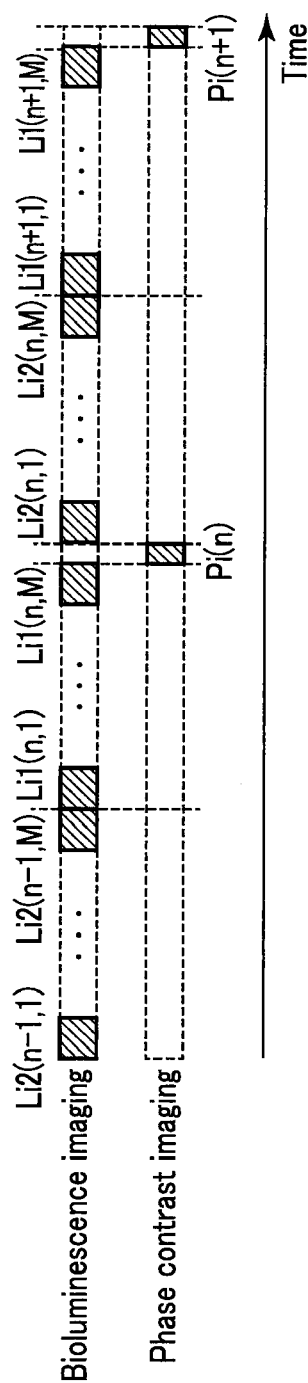
FIG. 6 is a chart showing an example of timing with which a phase contrast image Pi(n) and a bioluminescence image Li(n) are captured by the device.

More specifically, short-time exposure images are captured in the order presented below, as shown in FIG. 6:
Li2(n−1,1), . . . , Li2(n−1,M), Li1(n,1), . . . , Li1(n,M), Pi(n), Li2(n,1), . . . , Li2(n,M), Li1(n+1,1), . . . , Li1(n+1,M), Pi(n+1).

The bioluminescence image Li1(n,m) is captured in the order presented below: Li1(1,1), Li1(1,2), . . . , Li1(1,M), Li1(2,1), Li1(2,2), . . . , Li1(n,M), Li1(n+1,1), . . .

The bioluminescence image Li2(n,m) is captured in the order presented below: Li2(1,1), Li2(1,2), . . . , Li2(1,M), Li2(2,1), Li2(2,2), . . . , Li2(n,M), Li2(n+1,1), . . .

It is desirable that the exposure time of each of the bioluminescence images Li1(n,m) and Li2(n,m) be T·L/(2× M). These bioluminescence images Li1(n,m) and Li2(n,m) are transferred to the bioluminescence pseudo-long-time exposure image creation unit 320.

As described above, the bioluminescence pseudo-long-time exposure image creation unit 320 composes a plurality of short-time exposure images to falsely create an image corresponding to a long-time exposure image captured by picking up an image of a cell under the long-time exposure condition during an interval including periods before and after each of a plurality of points in time. More specifically, the bioluminescence pseudo-long-time exposure image creation unit 320 accumulates the bioluminescence images Li1(n,m) and Li2(n,m) (m=1 to M) to create a bioluminescence image Li(n) whose image pickup point in time falsely coincides with that of the phase contrast image Pi(n), and the bioluminescence image Li(n) is used for the subsequent tracking process. The bioluminescence image Li(n) is transferred to the second tracking unit 230.

The second tracking unit 230 tracks a cell on the basis of a pseudo-long-time exposure image created by the bioluminescence pseudo-long-time exposure image creation unit 320.

Figure 7:
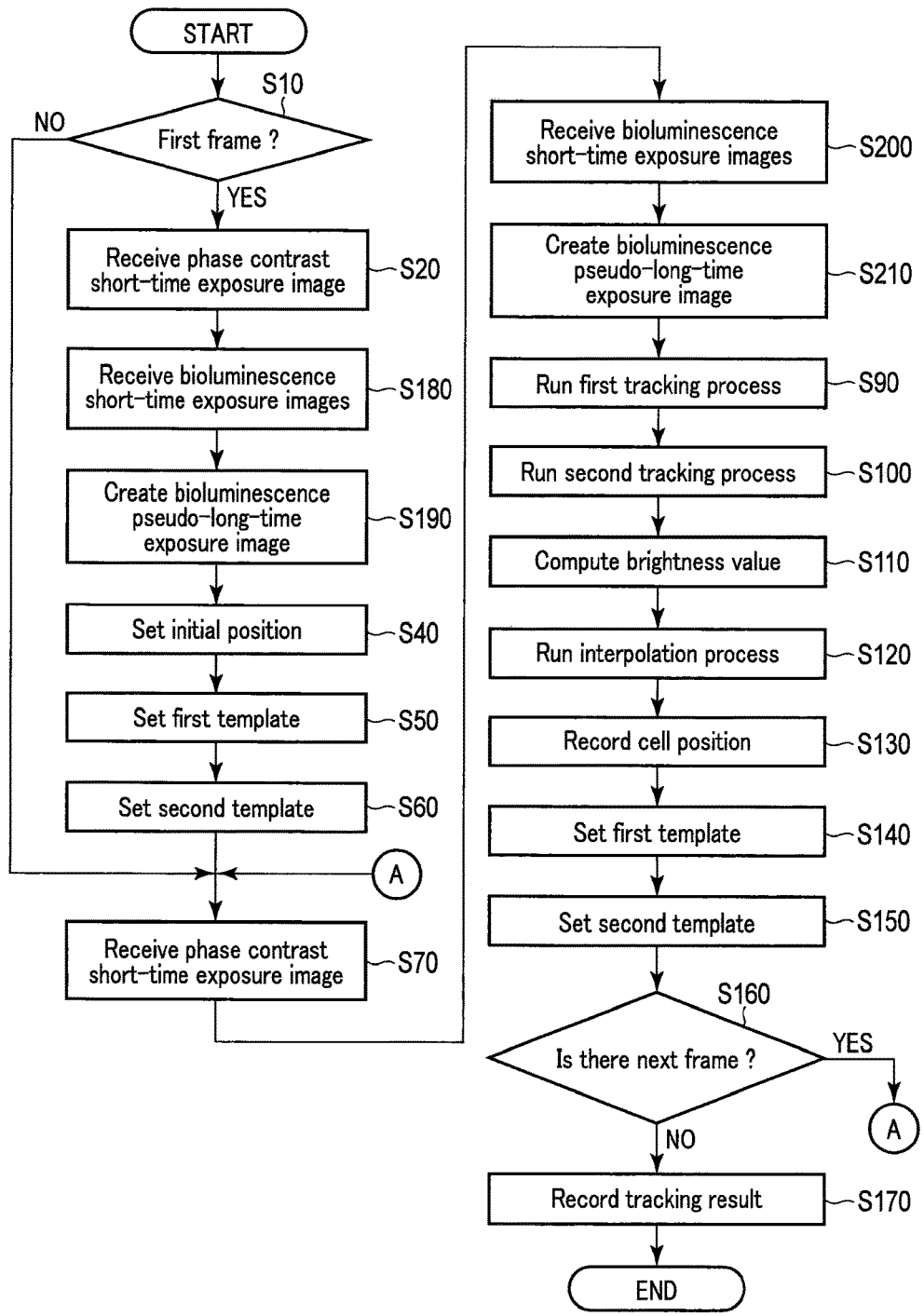
FIG. 7 is a cell tracking process flowchart in the device.

An example of the cell tracking process according to the second embodiment, which differs from the process according to the first embodiment, will be described in accordance with the cell tracking process flowchart shown in FIG. 7.

After the foregoing steps S10 and S20, in step S180, the bioluminescence pseudo-long-time exposure image creation unit 320 receives bioluminescence images Li1(1,m) and Li2(1,m).

In step S190, the bioluminescence pseudo-long-time exposure image creation unit 320 composes the bioluminescence images Li1(1,m) and Li2(1,m) to create a bioluminescence image Li(1) whose image pickup point in time falsely coincides with that of the phase contrast short-time exposure cell image Pi(1).

Next, after steps S40 to S70, in step S200, the bioluminescence pseudo-long-time exposure image creation unit 320 receives bioluminescence images Li1(n,m) and Li2(n,m).

In step S210, the bioluminescence pseudo-long-time exposure image creation unit 320 composes the bioluminescence images Li1(n,m) and Li2(n,m) to create a bioluminescence image Li(n) whose image pickup point in time falsely coincides with that of the phase contrast image Pi(n).

After that, the process in steps S70 to 5170 is performed using the bioluminescence image Li(1) created in the step S190 and the bioluminescence images Li(n) created in the step S210.

According to the second embodiment as described above, in order to capture a bioluminescence image Li(n), a plurality of bioluminescence images Li1(n) and Li2(n) are picked up by short exposure during an interval before and after an image pickup point in time of the phase contrast image Pi(n) as a reference, and the bioluminescence images Li1(n) and Li2(n) are composed. It is thus needless to say that the second embodiment brings about an advantage similar to that of the first embodiment. Furthermore, in the second embodiment, a bioluminescence image Li(n) whose image pickup point in time falsely coincides with that of the phase contrast image Pi(n) is created and used for a tracking process. It is thus possible to create a bioluminescence image Li(n) whose image pickup point in time falsely coincides with that of the phase contrast image Pi(n) and perform a tracking process without varying a cell position.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A cell tracking device comprising:
    a first image acquisition unit configured to pick up images of a cell under a short-time exposure condition at a plurality of points in time to capture a plurality of short-time exposure images;
    a second image acquisition unit configured to pick up images of the cell under a long-time exposure condition to capture long-time exposure images, each image of the cell under the long-time exposure condition being picked up within each interval between the plurality of points in time;
    a first tracking unit configured to track the cell based upon the short-time exposure images;
    a second tracking unit configured to track the cell based upon the long-time exposure images; and
    an interpolation unit configured to interpolate a tracking result obtained by the second tracking unit with a tracking result obtained by the first tracking unit.

2. The cell tracking device recited in claim 1, wherein the first image acquisition unit and the second image acquisition unit are configured to pick up images of the cell by observation methods of different microscopic methods.

3. The cell tracking device recited in claim 2, wherein the first image acquisition unit and the second acquisition unit include a selection unit which is configured to select one of the microscopic methods including a phase contrast microscope for picking up an image of the cell under the short-time exposure condition and the microscopic method including a bioluminescence microscope for picking up an image of the cell under the long-time exposure condition for each image pickup.

4. The cell tracking device recited in claim 1, wherein the second image acquisition unit is configured to pick up images of the cell under the short-time exposure condition to capture the plurality of short-time exposure images during an interval including periods before and after each of the plurality of points in time, and is configured to compose the plurality of short-time exposure images to falsely create an image corresponding to the long-time exposure image captured by picking up the cell under the long-time exposure condition during the interval including periods before and after the each of the plurality of points in time; and
    the second tracking unit is configured to track the cell based upon the long-time exposure image falsely created by the second image capturing unit.

5. The cell tracking device recited in claim 4, wherein when T is a predetermined point in time, I is a time interval and N is an integer of 0 or more,
    the second image acquisition unit is configured to pick up images of the cell under the short-time exposure condition to capture a plurality of short-time exposure images at a plurality of points in time during intervals $T+N\times I-(I/2)$ to $T+N\times I+(I/2)$ including periods before and after the plurality of points in time, and is configured to falsely create an image corresponding to the long-time exposure image captured by picking up an image of the cell under the long-time exposure condition during each of the intervals $T+N\times I-(I/2)$ to $T+N\times I-(I/2)$.

6. The cell tracking device recited in claim 1, wherein the interpolation unit is configured to select tracking of the cell by the second tracking unit if a brightness value of the long-time exposure image captured by the second image acquisition unit is equal to or larger than a predetermined threshold value, and is configured to select tracking of the cell by the first tracking unit if the brightness value is smaller than the predetermined threshold value.

7. The cell tracking device recited in claim 6, wherein the interpolation unit is configured to compare an average value of the brightness in the long-time exposure image and the predetermined threshold value, and is configured to select tracking of the cell by the second tracking unit if the average value of the brightness is equal to or larger than the predetermined threshold value, and to select tracking of the cell by the first tracking unit if the average value of the brightness is smaller than the predetermined threshold value.

8. The cell tracking device recited in claim 1, wherein the first image acquisition unit includes one of a phase contrast microscope and a differential interference contrast microscope.

9. The cell tracking device recited in claim 1, wherein the second image acquisition unit includes one of a bioluminescence microscope and a fluorescence microscope.

10. The cell tracking device recited in claim 1, wherein when T is a predetermined point in time, I is a time interval and N is an integer of 0 or more,
    the first image acquisition unit is configured to pick up images of the cell under the short-time exposure condition to capture the short-time exposure images at the plurality of points in time $T+N\times I$, and
    the second image acquisition unit is configured to pick up images of the cell under the long-time exposure condition to capture the long-time exposure images within the intervals $T+N\times I$ to $T+(N+1)\times I$ between the plurality of points in time.

11. A cell tracking method comprising:
    picking up images of a cell under a short-time exposure condition at a plurality of points in time to capture a plurality of short-time exposure images;
    picking up images of the cell under a long-time exposure condition to capture long-time exposure images, each image of the cell under the long-time exposure condition being picked up within each interval between the plurality of points in time;
    tracking the cell based upon the short-time exposure images;
    tracking the cell based upon the long-time exposure images; and
    interpolating a tracking result based upon the long-time exposure images with a tracking result based upon the short-time exposure image.

12. A storage medium non-transitory storing computer-readable cell tracking programs which are readable by a computer, the computer performing:
    a first image pickup function for picking up images of a cell under a short-time exposure condition at a plurality of points in time to capture a plurality of short-time exposure images;
    a second image pickup function for picking up images of the cell under a long-time exposure condition to capture long-time exposure images, each image of the cell under the long-time exposure condition being picked up within each interval between the plurality of points in time;
    a first tracking function for tracking the cell based upon the short-time exposure images;
    a second tracking function for tracking the cell based upon the long-time exposure images; and
    an interpolation function for interpolating a tracking result obtained by the second tracking function with a tracking result obtained by the first tracking function.

* * * * *